(12) United States Patent
Brandt et al.

(10) Patent No.: US 8,008,434 B2
(45) Date of Patent: Aug. 30, 2011

(54) PREPARATION OF SOLID PHASE BOUND PEPTIDES OR PNAS

(75) Inventors: Ole Brandt, Heidelberg (DE); Anette Jacob, Dossenheim (DE); Jörg Hoheisel, Wiesloch (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 846 days.

(21) Appl. No.: 11/597,693

(22) PCT Filed: May 25, 2005

(86) PCT No.: PCT/EP2005/005654
§ 371 (c)(1),
(2), (4) Date: Feb. 8, 2007

(87) PCT Pub. No.: WO2005/118616
PCT Pub. Date: Dec. 15, 2005

(65) Prior Publication Data
US 2008/0045694 A1  Feb. 21, 2008

(30) Foreign Application Priority Data
May 28, 2004 (EP) .................................... 04012691

(51) Int. Cl.
*C07K 17/00* (2006.01)
(52) U.S. Cl. .......................... 530/333; 530/334; 530/335
(58) Field of Classification Search .................. 530/333, 530/334, 335
See application file for complete search history.

(56) References Cited

U.S. PATENT DOCUMENTS

| | | | | |
|---|---|---|---|---|
| 4,432,877 | A | * | 2/1984 | Tzodikov ....................... 210/656 |
| 5,391,711 | A | * | 2/1995 | Funakoshi et al. ............. 530/344 |
| 5,420,246 | A | * | 5/1995 | Rutter et al. ................... 530/334 |
| 5,470,703 | A | * | 11/1995 | Nokihara et al. ................ 435/4 |
| 5,541,061 | A | * | 7/1996 | Fodor et al. ........................ 506/9 |
| 5,556,762 | A | * | 9/1996 | Pinilla et al. ....................... 506/5 |
| 5,738,996 | A | * | 4/1998 | Hodges et al. ..................... 506/9 |
| 6,075,127 | A | * | 6/2000 | Roggero et al. ................ 530/412 |

OTHER PUBLICATIONS

Krieger (Proc Natl Acad Sci 73(9), 3160-64, 1976).*
Brandt Ole et al., Nucleic Acids Research, Oct. 1, 2003, vol. 31, No. 19, p. e119.
Chan et al., 2000, FMOC Solid Phase Peptide Synthesis, A Practical Approach, XX, XX pp. 41-76.
Emili et al., Nature Biotechnology, Nature Pub. Co, New York, NY, vol. 18, No. 4, Apr. 2000, pp. 393-397.
Zhu et al., Current Opinion in Chemical Biology, vol. 5, No. 1, Feb. 2001, pp. 40-45.
Arlinghaus, et al., Appl Surf Sci; Applied Surface Science, Jun. 15, 2004, vol. 231-232, May 10, 2004, pp. 392-396.
Bauer et al., Tetrahedron Letters, Elsevier Science Publishers, Amsterdam, NL, vol. 44, No. 27, Jun. 30, 2003, pp. 5019-5023.
Matysiak et al., Biotechniques, Eaton Publishing, Natick, US, vol. 31, No. 4, Oct. 2001, pp. 896, 898, 900-902, 904.
Satish et al., Combinatorial Chemistry and High Throughput Screening, Hilversum, NL, vol. 5, No. 3, May 2002, pp. 253-259.
Merrifield et al., J. Am. Chem. Soc., vol. 85, pp. 2149-2154, (Jul. 1963).
Nielsen et al., Science, vol. 254, pp. 1497-1500, (Dec. 1991).
Jensen et al., Biochemistry, No. 36, pp. 5072-5077, (1997).
Zhang et al., Nucleic Acids Research, vol. 28, No. 17, pp. 3332-3338, (2000).
Petraccone et al., Biopolymers, vol. 73, pp. 434-442, (2004).
Blankmeyer-Menge et al., Tetrahedron Letters, vol. 31, No. 12, pp. 1701-1704,, (1990).
Sieber, Tetrahedron Letters, vol. 28, No. 49, pp. 6147-6150, (1987).
Chan et al., 2000, FMOC Solid Phase Peptide Synthesis, A Practical Approach, pp. 41-76.
Emili et al., Nature Biotechnology, vol. 18, No. 4, Apr. 2000, pp. 393-397.
Arlinghaus, et al., Applied Surface Science, Jun. 15, 2004, vol. 231-232, May 10, 2004, pp. 392-396.
Bauer et al., Tetrahedron Letters, vol. 44, No. 27, Jun. 30, 2003, pp. 5019-5023.
Matysiak et al., Biotechniques, vol. 31, No. 4, Oct. 2001, pp. 896, 898, 900-902, 904.
Satish et al., Combinatorial Chemistry and High Throughput Screening, vol. 5, No. 3, May 2002, pp. 253-259.

* cited by examiner

*Primary Examiner* — David Lukton
(74) *Attorney, Agent, or Firm* — Birch, Stewart, Kolasch & Birch, LLP.

(57) ABSTRACT

The invention relates to a process for the preparation of at least one solid phase bound peptide. PNA or a chimera.

26 Claims, 1 Drawing Sheet

PREPARATION OF SOLID PHASE BOUND PEPTIDES OR PNAS

Figure 1:
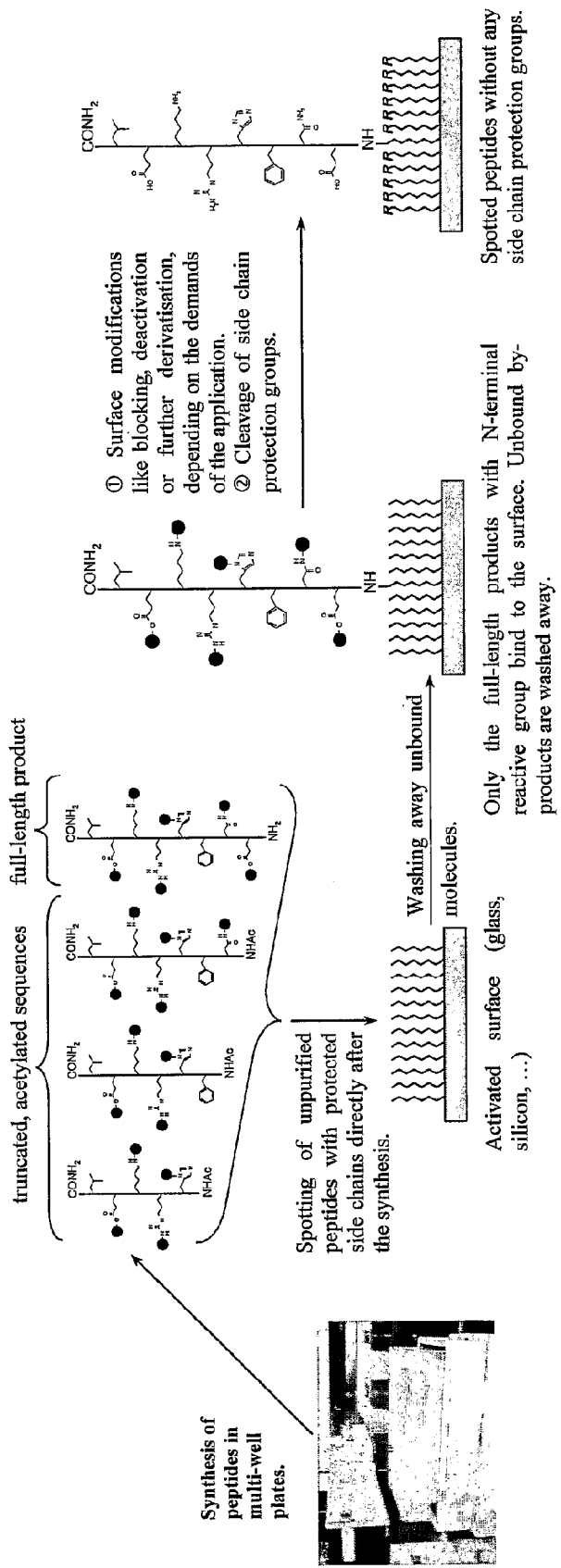

This application is a 371 of PCT/EP05/05654, filed May 25, 2005, which claims foreign priority to EPO 04012691.4, filed May 28, 2004.

The invention relates to a process for the preparation of at least one solid phase bound peptide, PNA or a chimera.

Solid phase peptide synthesis (SPPS) is a well established method. Merrifield et al. were the first who developed a convenient strategy for the build up of peptides by subsequently coupling amino acid monomers using a solid phase resin as a heterogeneous reaction medium (R. B. Merrifield, J. Am. Chem. Soc. 85 (1963) 2149-2154).

As a major advantage in comparison with the in-solution synthesis of peptides SPPS can be automated easily and impurities or by-products, reagents as well as unreacted starting material can be washed away while the product or intermediate remains tethered on the solid phase.

Normally the abovementioned Merrifield method starts with the attachment of the first C-terminal amino acid to a so called "linker" of a crosslinked polystyrene resin. The "linker" serves as a bridging element between the resin and the C-terminal amino acid of the peptide to be synthesized and the linker contains an acid sensitive bond to be used for the detachment of the peptide after synthesis.

As an example for a typical SPPS protocol the N-terminus can be protected with the 9-fluorenylmethoxycarbonyl (Fmoc) group, which is stable in acid, but removable by base. Any side chain functional groups are protected with base stable groups to make sure that only the N-terminal amino group incorporated in the peptide backbone can react-after removal of the Fmoc group-with the carboxylic acid group of the subsequent amino acid. As already mentioned the first step after the immobilization of the first amino acid is the deprotection of the amino function by removal of the Fmoc group using 20% piperidine in N,N-dimethylformamide (DMF). The amino function is coupled with an activated carboxylic acid via O-(Benzotriazol-1-yl)-N,N,N',N'-tetramethyluronium hexafluorphosphate (HBTU) ester of the next amino acid in the presence of a base to form a new amide bond. This process is repeated until the desired peptide is assembled at the resin. As a last step the complete peptide is cleaved from the resin using a solution containing trifluoroacetic acid (TFA). The released peptide in the solution can be precipitated and washed before further purification.

This "classic" method for SPPS was optimized in recent years using modified resins, linkers, protective groups, coupling chemistries and cleavage procedures but the principle remains the same.

Not only peptides can be synthesized in such a way. Also peptide nucleic acids (PNA) can be formed using the SPPS strategy. A PNA can be considered as a DNA analog where the deoxyribose backbone is replaced by a pseudo-peptide backbone. Each monomer has a nucleobase attached to the backbone. One such backbone consists of repeating units of N-(2-aniinoethyl) glycine linked through amide bonds (P. E. Nielsen et al., Science 254 (1991), 1497 and Biochemistry, 36 (1997), 5072). PNA is able to hybridize with a complementary nucleic acid fragment (DNA or RNA) to form a hybrid.

Advantageous applications due to the easy way of automation resulting from the immobilization of peptides or other macromolecules as well as small organic molecules are not limited to synthesis purposes. Solid phase carriers with molecules like peptides attached thereon are widely used in the fields of drug discovery, diagnostics and chromatography, just to mention a few. Such peptide solid phase carriers can be beads, glass fibers or capillary tubes. Planar carriers are often called "chips", "biochips" or "microarray" due to the potential of miniaturization.

There are two different approaches for the production of biochips or microarrays. On one hand the solid phase used for the synthesis of the peptide compounds is also used in the field of interest, e.g. for diagnostic purposes ("in-situ synthesis"). This strategy results in a high demand in relation to the properties of the solid phase, i.e. the carrier system must comply with the requisites for the synthesis and the diagnostic detection set up. Another disadvantage accompanies with the by-products also immobilized on the solid phase due to unreacted peptide fragments besides the peptide of interest. This problem is inherent for a system where the quantitative addition of a further monomer to the immobilized peptide chain is not ensured.

On the other hand the solid phase for the synthesis and the solid phase for the further application are different. The peptide is cleaved from the first solid phase resulting in a solution containing said peptide and more or less all fragments thereof as by-products. Before the product can be immobilized on a second solid phase a purification step is necessary. This process is the most common way but also disadvantageous because of the need of the separate purification step. Standard purification of peptides and PNAs is performed by RP-HPLC, which is labor and time consuming. Furthermore it is not well suited for high throughput synthesis. Due to miniaturization and screening methods, recently, many applications require small amounts of a huge number of purified molecules with different sequences. Therefore fast and easy purification of these molecules which can be done in parallel is desirable.

O. Brandt et al. (Nucleid Acids Research 31 (2003), e119) use PNA microarrays for the hybridisation of unlabelled DNA samples. The PNA molecules were synthesized using the acetyl group as capping agent for unreacted side products to prevent their immobilization onto the microarray after cleavage from the synthesis resin. Before the immobilization the PNA molecules were fully deprotected. This is disadvantageous because a flexible modification (like the deactivation of unreacted binding groups presented on the microarray for the immobilization of the PNA molecule via N-terminal groups) of the microarray is more or less impossible due to the reactivity of the side chain functional groups of the PNA molecules and thus the method can't be used when molecules include peptide units, i.e. amino acids having side chain functional groups, which are by far more reactive compared to the PNA molecules used. Derivatization of said side chain functional groups may occur.

Surprisingly, the inventors have found a new way for the preparation of solid phase bound peptides, PNAs or constructs with amino acid, PNA and other monomer units (herein called "chimera") using two different solid phases where the purification step takes place concomitantly during the immobilization of the products on the second solid phase and therefore the separate HPLC purification can be left out.

Thus, the object of the invention is to provide a new process for the preparation of solid phase bound peptides, PNAs or chimera where a separate purification step for the separation of previously bound by-products is not necessary. The present method is therefore particularly useful for the production of microarrays.

The general concept of the invention is based on the fact that after a coupling step remaining terminal groups that do not form the appropriate bond, i.e. remain unreacted, are blocked with a capping agent to prevent subsequent undesired coupling to another solid phase via terminal group of the complete sequence. While the terminal group of the peptide, PNA or chimera having a sequence of interest, i.e. the desired product, is deprotected to react with the second solid phase the undesired by-products are blocked and are unable to react with the second solid phase and can be washed away easily without tedious purification. The main advantage of the process is that standard solid phase synthesis protocols can be used.

Accordingly, the process of the invention for the preparation of at least one solid phase bound peptide, PNA or chimera having a sequence of interest comprises the steps of (a) immobilizing a starting sub-unit having a first protective group for the protection of the tail group on a first solid phase and subsequently deprotecting said tail group;
(b) coupling to the tail group of the previously immobilized sub-unit by an additional sub-unit bearing the first protective group for the protection of the tail group;
(c) blocking of unreacted tail groups of the previously immobilized sub-unit from step (b) with a capping group other than the first protective group;
(d) deprotecting the tail group bearing the first protective group;
(e) repeating steps (b) to (d) until completion of the sequence of interest;
(f) cleaving the peptide, PNA or chimera from the first solid phase under reaction conditions not affecting the capping group and immobilize the peptide, PNA or chimera via tail group without further purification on a second solid phase.

A sub-unit may have one or more additional side chain protective groups which are also not affected in step (f). These can be cleaved after having immobilized the peptide, PNA or chimera on the second solid phase and/or after deactivation or blocking of the second solid phase has taken place—if necessary. In case more than one side chain protective group is present, preferably all of them are not affected in step (f). However especially when side chain functional groups are present which are not capable of reacting with the second solid phase in step (f) and do not affect a derivatization of the second solid phase-if applicable-adversely the respective side chain protective group or groups may be cleaved in step (f).

Immobilizing side chain protected molecules is especially advantageous because otherwise deprotected functional groups of the side chains or bases, respectively, from both-products as well as blocked by-products—may bind to the second surface, thereby diminishing the purification effect. Another advantage for many applications is that products are immobilized solely via their tail group. Therefore all functional groups of the side chains which are later on deprotected are easily accessible for the reaction partners of the respective application. Additionally, the surface derivatization of the second solid surface (if necessary) can be adapted to the needs of the versatile applications without affecting the bound protected molecules. Deactivation or blocking of the surface with different reagents after immobilization of the protected products leads to surfaces with different adjustable properties (ionic, hydrophilic, hydrophobic surfaces). In that case cleavage of the side chain protecting groups takes place after surface adjustment. Thus, depending on the application, unspecific binding of the reaction partners to the second surface can be minimized.

Furthermore, it is especially advantageous to immobilize the peptide, PNA or chimera having any side chain functional group in a protected form to facilitate subsequent modification of the surface of the second solid phase by using reactive agents like acid chlorides for the deactivation (e.g. acetyl chloride, glutaric acide monoethyl ester chloride, mono-ethyl oxalyl chloride, palmitoyl chloride), anhydrides (e.g., acetic anhydride, 1-nahpthyl acetic anhydride, butyric anhydride, dodecanoic anhydride, citraconic anhydride) or activated esters (e.g. pentafluorophenyl (OPfp) esters of amino acids like Fmoc-Leu-OPfp, succinimidyl esters or other preactivated carboxylic acids and the like without affecting the side chain functional group of all types of molecules (peptides, PNA and chimera).

The side chain functional groups may be fully or selectively deprotected. The latter is preferred if subsequent modification of the peptide, PNA or chimera is desired, e.g. to prolongate the molecular chain or cross-link different strands immobilized on the second solid phase.

Each immobilization, coupling or capping step can be accompanied with a subsequent washing step to remove impurities or by-products, reagents as well as unreacted starting material not immobilized on the solid phase.

The process can be used for the synthesis of one or more solid phase bound peptides, PNAs or chimera. Due to its potential for automation the process is particularly suitable in parallel synthesis of a plurality of compounds, especially when using combinatorial chemistry. Combinatorial chemistry offers the best tools for the synthesis of so called libraries. The advantage of combinatorial chemistry, particularly the efficacy of automated parallel synthesis, lies in its ability to produce hundreds and thousands of compounds in a very short time frame.

The term "peptide" means a molecule that is formed using naturally occurring L-amino acids or analogs thereof, like D-amino acids or N-alkylated amino acids or the like. Preferred amino acids are selected from the group consisting of Ala, Arg, Asn, Asp, Cys, Glu, Gln, Gly, His, Hyl, Hyp, Ile, Leu, Lys, Met, Phe, Pro, Ser, Thr, Trp, Tyr, and Val. Also other building blocks are possible having a carboxylic acid and an amino group. Additionally, modifications like fluorescence dyes or biotin are possible.

The term "PNA" means a DNA analog where the deoxyribose backbone is replaced by a pseudo-peptide backbone. Each monomer has a nucleobase attached to the backbone. One such backbone may consist of repeating units of N-(2-aminoethyl)glycine linked through amide bonds.

As mentioned above the term "chimera" within the present invention means a molecule with an amide bond based backbone and side chains typically occurred in peptides as well as PNAs. Thus, a chimera comprises peptide monomers as well as PNA monomers (see e.g. X. Zhang et al., Nucleic Acids Res. 28 (2000), 3332). A chimera may also comprise DNA monomers resulting in a PNA-DNA chimera (see e.g. L. Petraccone et al., Biopolymers 73 (2004), 434) or peptide-DNA chimera where the backbone does not contain amide bonds exclusively. Preferably, no DNA monomer is incorporated in a chimera.

Normally, peptides and PNAs are formed using standard SPPS by adding one monomer, i.e. amino acid, after the other. Alternatively all or some of the reaction steps can be carried out using peptide, PNA or chimera fragments. Both, monomers and fragments can be summarized as sub-units.

In the first step of the inventive process the starting sub-unit is immobilized on a first solid phase. The fictional group reacting directly or indirectly with the solid phase can be considered head group, while the functional group opposite to the solid phase can be called tail group. Preferably, the head group is the C-terinal carboxylic acid group and the tail group is the N-terminal alpha-amino group of the amino acid or the primary amino group of N-(2-aminoethyl)glycine. Other suitable tail groups may be amino groups other than in alpha position or other functional groups like the thiol group.

To prevent a head-to-tail reaction of two sub-units instead of the immobilization the tail group is protected by a first protective group. This group is stable during the immobilization procedure but can be cleaved for the subsequent coupling step.

The use of protective group in synthesis, especially in solid phase synthesis and in particular for SPPS is well established in the art. A person skilled in art can easily find out appropriate protective groups that match the requirements for the particular molecule (peptide, PNA or chimera). In general, suitable protective groups are listed together with their abbreviations below (see Novabiochem Combinatorial Chemistry Catalog&Solid Phase Organic Chemistry Handbook, Mar. 98, Callbiochem-Novobiochem AG, Switzerland): Acetamidomethyl (Acm), Acetyl (Ac), Adamantyloxy (AdaO), Benzoyl (Bz), Benzyl (Bzl), Benzyloxy (BzlO), Benzyloxycarbonyl (Z), Benzyloxymethyl (Bom), 2-Bromobenzyloxycarbonyl (2-Br-Z), tert.-Butoxy (tBuO), tert.-Butoxycarbonyl (Boc), tert.-Butoxymethyl (Bum), tert.-Butyl (tBu), tert.-Buthylthio (tButhio), 2-Chlorobenzyloxycarbonyl (2-Cl—Z), Cyclohexyloxy (cHxO), 2,6-Dichlorobenzyl (2,6-DiCl-Bzl), 4,4'-Dimethoxybenzhydryl (Mbh), 1-(4,4-Dimethyl-2,6-dioxo-cyclohexylidene)3-methyl-butyl (ivDde), 4-{N-[1-(4,4-Dimethyl-2,6-dioxo-cyclohexylidene)3-methylbutyl]-amino) benzyloxy (ODmab), 2,4-Dinitrophenyl (Dnp), Fluorenylmethoxycarbonyl (Fmoc), Formyl (For), Mesitylene-2-sulfonyl (Mts), 4-Methoxybenzyl (MeOBzl), 4-Methoxy-2,3,6-trimethyl-benzenesulfonyl (Mtr), 4-Methoxytrityl (Mmt), 4-Methylbenzyl (MeBzl), 4-Methyltrityl (Mtt), 3-Nitro-2-pyridinesulfenyl (Npys), 2,2,4,6,7-Pentamethyldihydrobenzofurane-5-sulfonyl (Pbf), 2,2,5,7,8-Pentamethyl-chromane-6-sulfonyl (Pmc), Tosyl (Tos), Trifluoroacetyl (Tfa), Trimethylacetamidomethyl (Tacm), Trityl (Trt) and Xanthyl (Xan). To protect PNAs the Benzhydryloxycarbonyl Bhoc group is well established. This list is non-limiting and can be completed readily by a person skilled in the art.

In case the side chains of the sub-units contain additional functional groups, like e.g. additional carboxylic, amino, hydroxy or thiol groups further protective groups are necessary. If the Fmoc strategy for the tail group is used, Mtr, Pmc, Pbf for the protection of Arg can be used, Trt, Tmob, can be used for Asn, Gln; Boc can be used for Trp and Lys; tBu for Asp, Glu, Ser, Thr and Tyr and Acm, tBu, tbuthio, Trt and Mmt can be used for the protection of Cys. For PNA monomers the Bhoc group is used for A, C and G. In the BOC/Bzl strategy Bzl is used for the protection of Asn, Gln, Asp, Glu, Ser, Thr and Tyr while 2-Cl—Z is used for Lys; Tos, Mts, Mbs can be used for Arg; Tos, Bum Bom, Trt for His and tBu, MeBzl, Mob and Acm can be used for the protection of Cys. These are only some of the possible combinations used in SPPS. For a person skilled in the art other suitable combinations are obvious.

In a preferred embodiment of the present invention the Fmoc group is used as a first protective group and can be cleaved using piperidine.

The first solid phase used for synthesis can be a synthetic resin, a synthetic polymer film or a silicon or silicate surface, e.g. controlled pore glass (CPG), suitable for synthesis purposes. Preferably, a resin is used. The starting sub-unit may be connected to the first solid phase either directly or, preferably, via a linker. Normally, synthesis resins are commercially available and already functionalized with an appropriate linker (see e.g. Novabiochem Combinatorial Chemistry Catalog & Solid Phase Organic Chemistry Handbook, March 98, Callbiochem-Novobiochem AG, Switzerland). Linkers include weak bonds that can be cleaved easily to remove the product for the solid phase in the final reaction step of the solid phase synthesis. Linkers may be cleavable under acidic or basic conditions, using hydrogen or photolytically or otherwise. As a pre-requisite the cleavage conditions are different to those for deprotecting the tail group. For a person skilled in the art it is obvious to select appropriate resin-linker systems.

2-Chlortrityl resin, an acid labile resin, is commonly used to cleave a product from the resin without cleaving the protective groups. Photolable resins are useful because cleavage is carried out without using acidic or basic conditions and therefore basic- and acid-lable protective groups at side chains remain stable. Brominated Wang resin, Anp resin and Fmoc-photolable resin are examples of this class.

Resins are often based on polystyrene or polystyrene-polyethyleneglycole.

Examples of resins functionalized with linkers suitable for the Boc-chemistry are Oxime resin SS, phenol resin, brominated Wang resin and brominated PPOA resin. Using Fmoc chemistry for the protection of the tail group appropriate resins are AMPB-BHA resin, Sieber Amide resin, Rink Acid resin, Tentagel S AC resin, 2-Chlorotrityl Chloride resin, 2-Chlorotrityl Alcohol resin, TentaGel S Trt-OH resin, Knorr-2-Chlorotrityl resin, Hydrazine-2-Chlorotrityl resin, ANP resin, Fmoc photolable resin, HMBA-MBHA resin, TentaGel S HMB resin, Aromatic Safety Catch resinBAl resin and Fmoc-Hydroxylamine 2 chlorotrityl resin. Other suitable resins are PL Cl-Trt resin, PL-Oxime resin and PL-HMBA Resin. Preferably, the first solid phase is a Rink acid resin or a HMBA-MBHA resin.

For each resin appropriate coupling conditions are known in the literature for the attachment of the starting monomer or sub-unit.

The coupling is preferably performed using an MSNT (1-(Mesitylene-2-sulfonyl)-3-nitro-1H-1,2,4-triazole) method (see Novabiochem catalogue 2000, page S33 or B. Blankenmeyer-Menge et al. Tetrahedron Lett. 31 (1990), 1701). An alternative coupling method uses 2,6-dichlorobenzoylchloride activation (P. Sieber, Tetrahedron Lett. 28 (1987), 6147).

As a second step after immobilizing the starting sub-unit including the deprotection of the tail group, the coupling of a subsequent sub-unit (also with the first protective group for the tail group) is carried out in a "head-to-tail manner". Mostly, the carboxylic group as head group is activated in the presence of an activating reagent.

Preferably, standard solid phase synthesis protocols are used for the coupling step. Especially suitable are coupling methods using HBTU (2-(1H-Benzotriazole-1-yl)-1,1,3,3-tetramethyluronium hexafluorophosphate) or HATU (2-(1H-7-Azabenzotriazol-1-yl)-1,1,3,3-tetramethyl uronium hexafluorophosphate).

Although, convenient methods were developed to form an amide bond (or other covalent bonds) quantitatively some of the tail groups remain unreacted. This results in a mixture of molecules attached to the first solid phase: Firstly, the product with a first protective group for the tail group; secondly, fragments of the product (and therefore by-product), where one or more coupling steps failed in the synthesis procedure, i.e. one or more monomers are missing.

In case the last coupling step was successful these by-products also bear a first protective group for the tail group, and thirdly by-products that do not have said first protective group. In case this mixture is cleaved from the solid phase a tedious purification step is necessary to separate the product from all other products. Otherwise the tail groups of the product as well as the tail groups of the by-products will react with a second solid phase.

This problem can be overcome in adding a separate step after the usual coupling step which step serves for the blocking of unreacted tail groups with a capping group that is other than the first protective group. The capping group is selected in that the cleavage of the first protective group does not affect the capping group, i.e. the capping group is stable under conditions used to deprotect the tail group having the first protective group.

Preferably, the capping group is a small reactive group. In a preferred embodiment the capping group is an Acetyl group.

This results in two groups of molecules—the product being blocked with the first protective group and by-products being blocked with the capping group.

As a next step for the inventive process the first protective group is cleaved to proceed with the coupling of next subunits. This coupling-blocking (capping)-deprotecting (of the first protective group) procedure is repeated until the sequence of interest is completed.

Finally, the mixture is cleaved from the first solid phase under reaction conditions not affecting the capping group, i.e. where the capping group is and additional side chain protective groups are stable, and immobilize the product via tail group without further purification on a second solid phase.

Before immobilizing the product the first protective group is subject to cleavage. This is accomplished simultaneously with the cleaving step from the solid phase or before the cleaving step. Due to the fact that by-products are blocked with the capping group and possible reactive side chains are protected the second immobilization is only successful for the product via tail group. The by-products can be removed easily, e.g. by washing them away.

Preferably, the release of the product is carried out using acidic, alkaline or photolytic conditions or by esterification. More preferred is the use of Trifluoroacetic acid (TFA), acetic acid (e.g. when using Rink acid resin), diluted TFA (e.g. when using Sieber resin) or NAOH, hydrazines, amines or sodium alkoholates.

The coupling to the second solid phase can include an activation step for the tail group or for the corresponding functional group on the solid phase. As the tail group is preferably an amino function the second solid phase can comprise carboxylic acid groups for which several activating reactions and agent are known. In general, the attachment to the second solid phase may be covalently, by adsorption, by forming a complex or ionic pair or otherwise; the covalent attachment is preferred.

Additionally the tail group may react with a further molecule to provide another functional group for the attachment to the solid phase via a solid phase functional group. Suitable pairs of corresponding functional groups are selected from the group consisting of thiol-maleimide, amino-succinimide, amino-aldehyde; and biotin-streptavidine.

As a convenient way to immobilize the product on the second solid phase standard techniques like spotting in case of planar supports or pipettes can be used.

The choice of the second solid phase depends on the further application. The second solid phase may be a polymer, silanized glass or silicon, membranes, porous surfaces or a gold surface.

The second solid phase can be in form of glass fibers, capillary tubes, beads or, preferably of a planar microarray or multi-well plate, where different peptides, PNAs or chimera are located in a two-or three-dimensional array format.

Such beads, microarrays or other solid phases may be used for the detection of interactions between the immobilized product and targets like proteins, DNA, RNA or the like or for purification of nucleic acids or for other applications in the fields of drug discovery, diagnostics and chromatography. In a preferred embodiment the microarray may be used for epitope mapping.

Optionally, depending on the application the second surface can be deactivated or derivatized, before the deprotection of the side chain groups of the immobilized products takes place as outlined before.

The following examples illustrate the invention but should not be construed as being limiting.

The following exemplary workflow for the preparation of peptide arrays is depicted in FIG. 1. Fully protected peptides are synthesized for example in multi well plates with frits in each well, using standard protocols. During each cycle, not extended products are acetylated. Finally the products are cleaved from the resin, whereby the side chain protection groups remain bound. Without further purification, the crude products are spotted onto an activated surface (for example succinimidyl ester activated surfaces for peptides with a termninal amino function). As all truncated sequences are acetylated and all functional groups (—OH, —SH, —$NH_2$) of the side chains of both, the acetylated by-products as well as the full length product remain fully protected, solely the product itself binds covalently via its terminal functional group to the surface. All by-products can easily be washed away, thereby allowing fast and easy purification of many samples in parallel. Due to the fact that the bound products are still protected, surface chemistry can be adapted to the needs of the following application. (Depending on the application, ionic, hydrophilic or hydrophobic surfaces may be advantageous to minimize unspecific binding of the reaction partners of the assay to the solid surface.)

Finally the side chain protection groups are cleaved from the bound molecules, leading to high quality arrays with functional peptides.

Synthesis of Protected Peptides

Synthesis of protected peptides was performed automatically by an AutoSpot robot (INTAVIS Bioanalytical Instruments AG, Cologne, Germany) in 96-well plates that have a frit in each well. A vacuum was applied to remove the reagents from the wells during the synthesis cycles. The Fmoc-protected NovaSyn TG Sieber resin (substitution of 0.1-0.2 mmol/g) was swelled for 1h in N,N-dimethylformamide (DMF) (2 mg resin per 100 µl). The solution was thoroughly mixed and a volume of 100 µl was distributed to each well for a standard scale synthesis. After extraction of DMF, Fmoc protection groups were removed from the resin by successive 1 min and 5 min incubations with 30 µl 20% (v/v) piperidine in DMF, with one DMF washing step in between. The resin was then washed five times with 80 µl DMF followed by the first coupling reaction. Per well, a volume of 4 µl of the Fmoc-protected monomer (amino acids, linkers or other derivatives; each 0.5 M in 1-methyl-2-pyrrolidone (NMP)), was activated for 60 sec with 4 µl HBTU (0.5 M in DMF) and a 3 µl mix of N,N-diisopropylethylaniine (DIEA, 0.67 M) and 2,6-lutidine (1 M) in DMF. Subsequently, the resin in each well was incubated with this mixture at room temperature for 20 min. Coupling was repeated after rinsing with DMF in between. The resin was then washed three times with DMF. For the capping of free, not elongated amino groups, there was an incubation with 5% acetic anhydride and 6% 2,6-lutidine in DMF for 5 min. Finally, the resin was washed another five times with 80 µl DMF. Deprotection, coupling of the next monomer and capping were repeated as described above until synthesis of the Peptide-molecule was completed.

Prior to cleaving the products from the resin, they were washed five times with 80 µl DMF followed by three washing steps with 80 μl 1,2-dichloroethane. After the resin was dried, cleavage took place by repetitive treatment with 100 μl 1% trifluoroacetic acid (TFA) in 1,2-dichloromethane. To avoid evaporation, nitrogen pressure rather than a vacuum was used to transfer the cleaved products into another 96-well plate wherein each well was pre-filled with 20 μl of 20% pyridine in methanol. The resin was washed with dichloromethane and methanol and the products were either lyophilized directly or the combined mixtures were evaporated under reduced pressure to 5% of their volume and then precipitated with ice cold water.

Each crude peptide product was redissolved in 100 μl water/dimethyl sulfoxide (1:1 or 1:2) and stored at 4° C.

Immobilization and Purification of the Products and Surface Deactivation

Crude products were diluted with water/dimethyl sulfoxide (1:1 or 1:2) and then spotted on succinimidyl ester activated aminosilane glass slides which were prepared using standard protocols (see below). After spotting, the slides were incubated at room temperature overnight. Deactivation of the surface was carried out in a solution of 50 mM succinic anhydride and 150 mM 1-methylirnidazole (NMI) in dichloroethane, each slide shaken in 15 ml for 2 h. (Depending on the subsequent application, the surface can also be deactivated or blocked by treatment with acetic anhydride or other reagents. As all bound peptides are fully protected, surface derivatisation can be adapted to the needs (ionic, hydrophilic or hydrophobic surrounding in order to avoid unspecific binding of the reaction partners). Finally the glass slides were washed thoroughly with dichloroethane, dimethyl sulfoxide and ethanol.

Cleavage of the Protection Groups:

In order to cleave the side chain protection groups of the bound peptides, the slides were immerged in 95% trifluoroacetic acid/5% triisopropylsilane for 20-30 min at room temperatur. After washing with dichloromethane, ethanol, water and ethanol, they were dried with a stream of nitrogene and stored at 4° C. until use.

Standard Protocol for Surface Derivatisations:

Silanisation: Untreated glass slides were etched in 10% NaOH (w/w) at room temperature for 1 h, followed by sonification for 15 min. After washing the wafers thoroughly with water and ethanol, they were incubated by shaking gently in a silanisation solution of 1 ml [3-aminopropyl]triethoxy silane in 20 ml 95% ethanol for 1 h and additional 15 min in an ultrasonic bath. Finally, the wafers were rinsed twice with ethanol, once with water, dried under a stream of nitrogen and heated to 110° C. for 20 min.

Succinimidyl Ester Activation:

Aminosilane-modified silicon wafers were immersed in a solution made of 150 mg N,N'-disuccinimidyl carbonate (DSC) and 0.5 ml DIEA in 14.5 ml dried acetone on a shaker at room temperature for 2 h, washed twice with 15 ml dried acetone and twice with 15 ml dichloroethane. The dried wafers were directly taken for the spotting procedure.

The invention claimed is:

1. A process for the preparation of at least one solid phase bound peptide, PNA or chimera having a sequence of interest with side chain functional groups comprising the steps
   a. immobilizing a starting sub-unit having a first protective group for the protection of the tail group on a first solid phase and one or more additional side chain protective groups for the protection of any side chain functional group if present in the sub-unit and subsequently deprotecting said tail group;
   b. coupling to the tail group of the previously immobilized sub-unit by an additional sub-unit bearing the first protective group for the protection of the tail group and one or more additional side chain protective groups for the protection of any side chain functional group if present in the sub-unit;
   c. blocking of unreacted tail groups of the previously immobilized sub-unit from step (b) with a capping group other than the first protective group;
   d. deprotecting the tail group bearing the first protective group;
   e. repeating steps (b) to (d) until completion of the sequence of interest;
   f. cleaving the peptide, PNA or chimera from the first solid phase under reaction conditions not affecting the capping group and not affecting at least one side chain protective group and immobilize the peptide, PNA or chimera via tail group without further purification on a second solid phase; and
   g. cleaving the one or more side chain protective groups after having immobilized the peptide, PNA or chimera on the second solid phase,
   wherein the tail group is an amino group.

2. The process according to claim 1, wherein prior to step (g) the surface of the second solid phase is modified.

3. The process according to claim 2, wherein the modification is carried out using acid chlorides, anhydrides, activated esters or preactivated carboxylic acids.

4. The process according to claim 1, wherein the one or more side chain protective groups are fully or selectively cleaved.

5. The process according to claim 1, wherein each immobilization, coupling or capping step is accompanied with a subsequent washing step.

6. The process according to claim 1, wherein the starting sub-unit is immobilized via a linker to the first solid phase.

7. The process according to claim 1, wherein the sub-unit is a monomer.

8. The process according to claim 1, wherein the immobilization of the first sub-unit is carried out using an MSNT (1-(Mesitylene-2-sulfonyl)-3-nitro-1H-1,2,4-triazole) method.

9. The process according to claim 1, wherein a plurality of solid phase bound peptides, PNAs or chimera are prepared in parallel.

10. The process according to claim 9, wherein the plurality of solid phase bound peptides, PNAs or chimera are prepared using combinatorial chemistry.

11. The process according to claim 1, wherein the first protective group is an Fmoc group.

12. The process according to claim 1, wherein the first protective group is cleaved using piperidine.

13. The process according to claim 1, wherein the capping group is an acetyl group.

14. The process according to claim 1, wherein the coupling is carried out using HBTU (2-(1H-Benzotriazole-1-yl)-1,1,3,3-tetramethyluronium hexafluorophosphate) or HATU (2-(1H-7-Azabenzotriazol-1-yl)-1,1,3,3-tetramethyl uronium hexafluorophosphate).

15. The process according to claim 1, wherein the peptide, PNA or chimera is cleaved from the first solid phase under acidic, alkaline or photolytic conditions or by esterification.

16. The process according to claim 15, wherein the peptide, PNA or chimera is cleaved from the first solid phase using TFA, diluted acetic acid, NaOH, hydrazines, amines or alkoholates.

17. The process according to claim 1, wherein the second solid phase is a bead, a multi-well plate, a membrane, a glass fiber or a capillary tube.

18. The process according to claim 1, wherein the second solid phase is a silanized glass or silicon, a polymer, a porous surface or a gold surface.

19. The process according to claim 17, wherein the peptide, PNA or chimera is immobilized on the second solid phase by spotting.

20. The process according to claim 1, wherein the peptide, PNA or chimera is covalently attached to the second solid phase.

21. The process according to claim 1, wherein the second solid phase is a planar microarray.

22. The process according to claim 1, wherein the second solid phase is an aminosilane-modified glass.

23. The process according to claim 1, wherein the tail group is an amino group.

24. The process according to claim 1, wherein the coupling is carried out using BBTU (2-(1H-Benzotriazole-1-yl)-1,1,3,3-tetramethyluronium hexafluorophosphate).

25. The process according to claim 1, wherein the process is used to prepare a solid phase bound peptide.

26. The process according to claim 1, wherein the first solid phase comprises styrene bearing a $C_{1-5}$ alkylamino group.

* * * * *